United States Patent [19]

Richardson

[11] Patent Number: 5,046,949
[45] Date of Patent: Sep. 10, 1991

[54] ARTICULAR SUPPORT SYSTEM FOR DENTAL MODELS

[75] Inventor: Terry A. Richardson, St.Charles, Ill.

[73] Assignee: C. J. Star Enterprises, Inc., St. Charles, Ill.

[21] Appl. No.: 588,755

[22] Filed: Sep. 27, 1990

[51] Int. Cl.⁵ ............................................. A61C 11/02
[52] U.S. Cl. ........................................ 433/57; 433/61
[58] Field of Search ..................... 433/53, 54, 55, 56, 433/57, 58, 59, 60, 61, 62, 63, 64, 65, 66, 67

[56] References Cited

U.S. PATENT DOCUMENTS

| 118,242 | 8/1871 | Hoffstadt | 433/65 |
|---|---|---|---|
| 321,457 | 7/1885 | Smith | 433/65 |
| 981,430 | 1/1911 | Kennedy | 433/60 |
| 3,078,577 | 2/1963 | Prentiki | 433/60 X |
| 4,175,325 | 11/1979 | Beckwith | 433/60 X |

FOREIGN PATENT DOCUMENTS 0744402  5/1956  United Kingdom .................. 433/56

Primary Examiner—John J. Wilson
Assistant Examiner—Jeffrey A. Smith
Attorney, Agent, or Firm—John L. Schmitt

[57] ABSTRACT

An articular support system for dental model sets includes a fixture having an upper portion carried by a lower base portion. The base portion has a base plate which connects with an inner support post. This post is formed with a vertically extending inner passageway. The upper portion includes an inner and outer plate connected by a releasable hinge. To use the system a base of a dental model of a person's upper teeth and lower teeth are each molded with front and rear indentations. Each model then fits into a bracket having spaced apart end walls. On an inner side of each end wall is a locking tab that fits into the respective model indentations. The lower teeth model bracket next is affixed to the fixture base plate with mastic. The upper model teeth then are placed in contact with the lower model teeth to reproduce the bit that occurs in the person's mouth. Next, the upper portion inner plate is loosely positioned in the base portion post passageway. With the outer plate positioned on top of the upper teeth model bracket, the plate and bracket are joined together with mastic. Lastly, the upper portion inner plate is secured with mastic in the post passageway. During preparation of crowns, dentures and like appliances, the models may be readily removed from the fixture and then reattached with the bite positioning accurately and reliably reproduced.

11 Claims, 3 Drawing Sheets

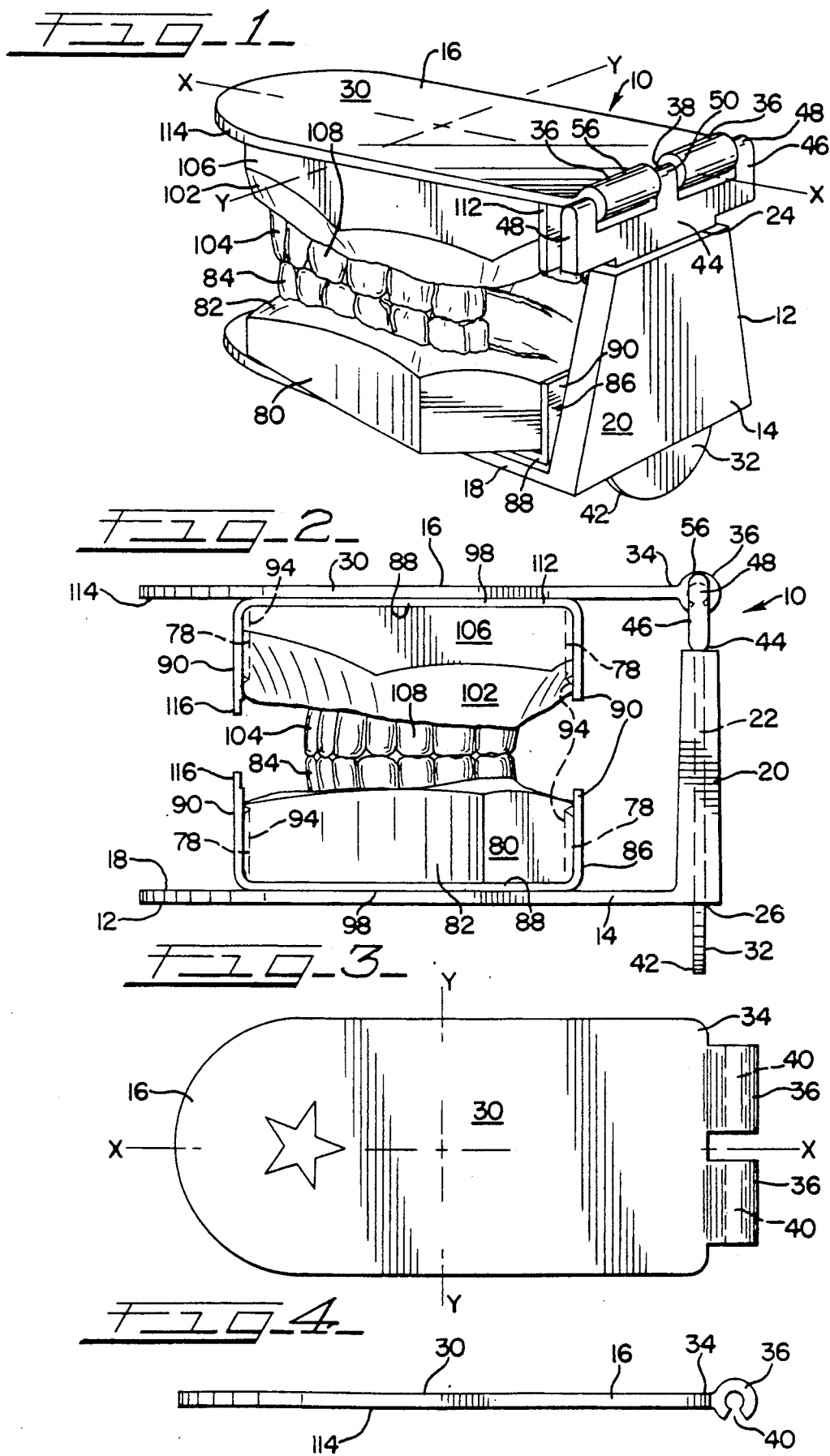

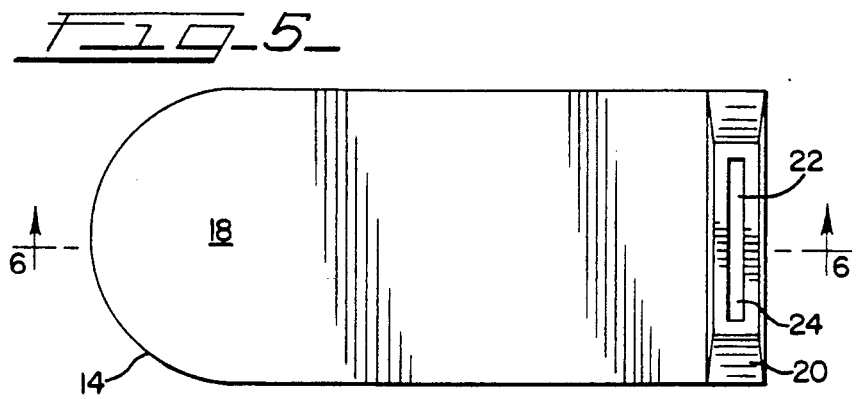
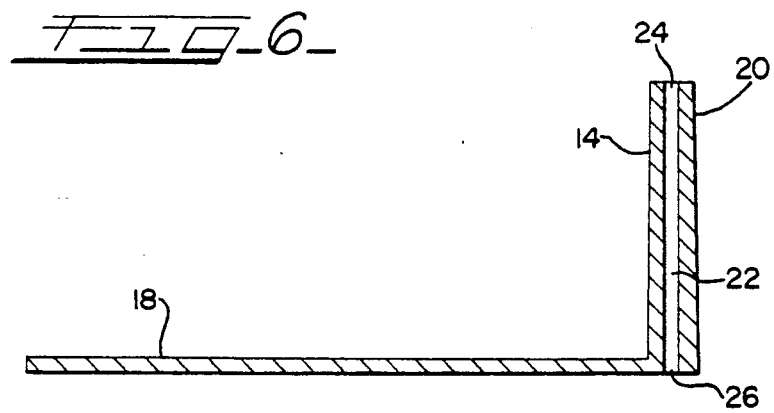
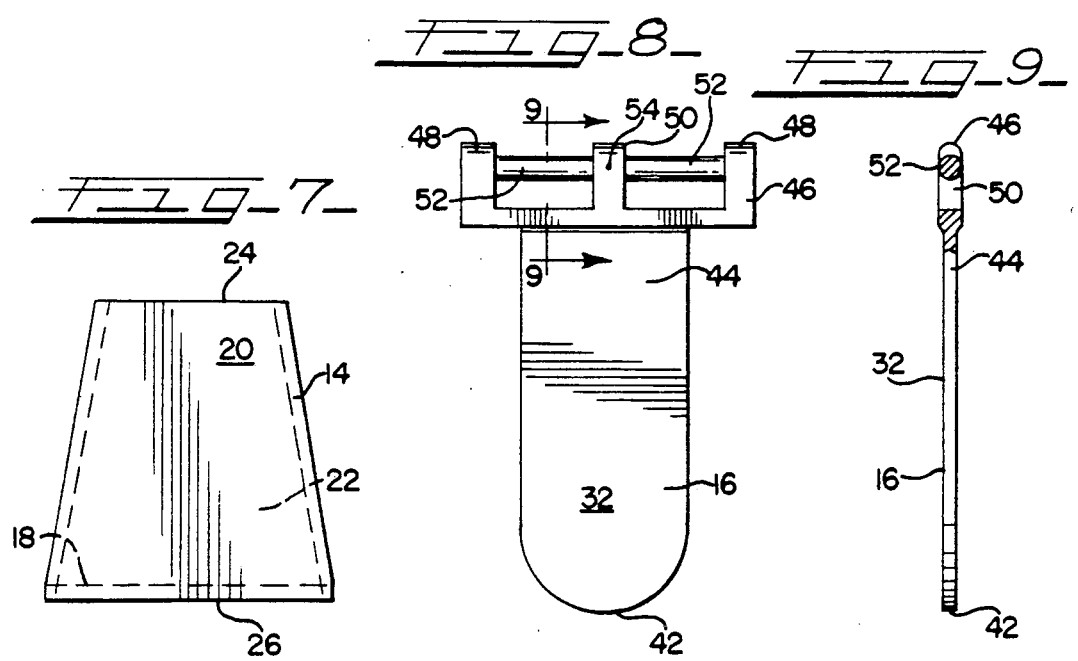

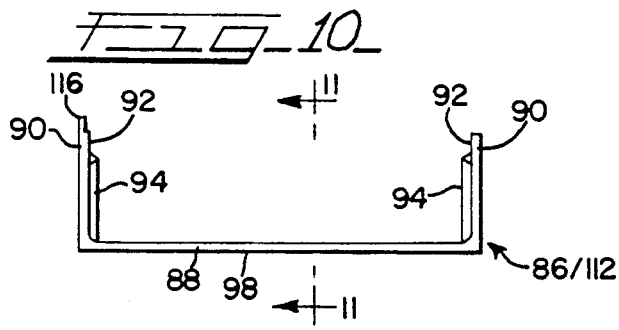
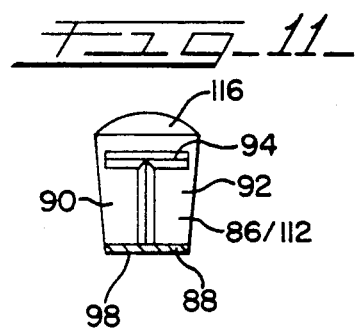
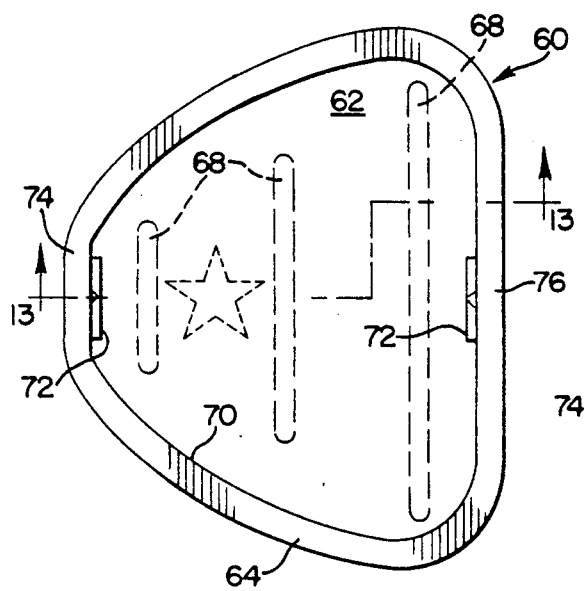
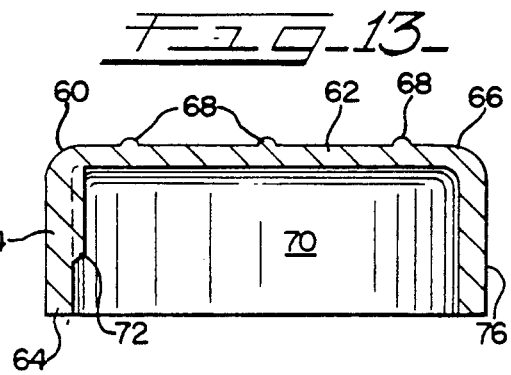
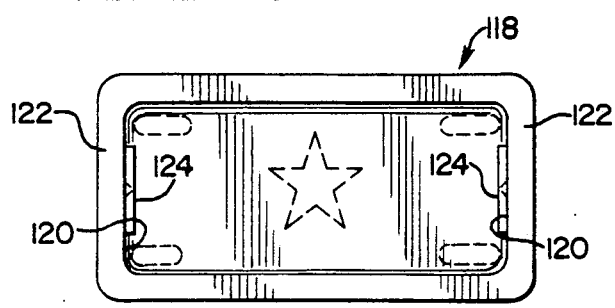
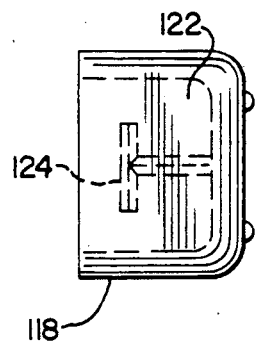

ARTICULAR SUPPORT SYSTEM FOR DENTAL MODELS

BACKGROUND OF THE INVENTION

1. Field of Invention

This invention relates generally to articular support systems for dental models and more particularly to a system that allows ready removal of an attached model and then its reattachment in a near exact same position so that the bite positioning between the upper and lower teeth of the models is readily and reliably recreated.

2. Prior Art

Articular supports for dental models are well known having been in use for many years.

One early articulator is set out in U.S. Pat. No. 2,348,606 wherein the models are attached by screws to a fixture of the articulator.

A more recent dental model support device is disclosed in U.S. Pat. No. 3,808,689 and includes a frame having an upper and lower platform. Each platform includes an outer looped-shaped portion to which a tray may be attached. Each tray in turn is formed with a wedged-shaped keyway slot to receive a complementarily shaped key formed as part of a base of a model of a dental impression. This key-slot arrangement allows the models to be readily attached to or removed from the support device.

Another recent dental model support arrangement is set out in U.S. Pat. No. 3,823,476. In this arrangement a base of each dental model is formed having a tray-like shape. On an inner side of a rear wall of each base tray is a channel-shaped glide formation to receive end plates of a hinge. With the model upper and lower teeth in their bite position, the hinge end plates may be affixed in their respective channel guides with mastic. As required, the models may be rotated apart.

U.S. Pat. No. 4,382,787 discloses a still further dental model articulator which is used widely today. This articulator includes a pair of U-shaped brackets having arms that are releasably hinged together. On a base of each bracket is a spherical member that may be pressed into a like-shaped depression on a mounting bracket. An outer end of each mounting bracket in turn is molded into a base of a respective dental model. With the teeth of the models in their bite position mastic is applied to each spherical connection to affix its location. The releasable hinge connection allows the models to be separated and then reconnected as required.

SUMMARY OF THE INVENTION

A dental model articular support system of this invention includes a fixture having a base portion. This base portion includes a base plate having a connecting vertical, inner support post. This post has a wedge-like shape and is formed with a like-shaped inner passageway having top and bottom openings.

The support system fixture further includes an upper portion comprising an inner and outer plate connected by a full-width, releasable hinge. An outer edge of the inner plate is arcuate shaped.

To use the system impressions first are made of a person's upper and lower teeth, for example. Each impression then may be formed into a model by filling a base mold and the impression with a gypsum paste and placing these together until the material has cured. Those teeth that are to be replaced by a denture or crowned may be made removable from the base of the model. The remaining teeth typically are integrally joined to the base.

The base mold is made of an elastomeric material and has a surrounding wall. On an inner surface of a front and rear portion of this wall is a pair of projections. These projections produce like-shaped impressions in a sidewall of the model base.

Each model then is fitted into a plastic holding bracket having end walls formed with inward facing locking tab. These tabs snap into the impressions of the model base. The lower model bracket next is attached to the base plate of the fixture with mastic.

The upper teeth of that model then are placed on the teeth of the lower jaw model to duplicate the bite positioning of the teeth. With the inner plate of the fixture upper portion positioned in the base post passageway and the outer plate seated flush against the upper teeth model bracket, these plates are secured in place with mastic.

The dental model support system of this invention provides several advantages over other such systems known or in use.

A first advantage of the system is that a dental model may be removed readily from any attached device, in this case its holding bracket. Thus, a model is easy to make, and there is no external structure to interfere with handling of the model, for example when external grinding or polishing of a cap for a tooth of the model is required.

A second advantage is that the models may be readily attached to the fixture while the teeth of the models are in their bite position. When the model teeth are in this bite position, a top surface of the base of the upper teeth model typically is not level. As a first step to complete this attachment, the model of the lower teeth is secured rigidly to the fixture. Then, the outer plate of the fixture upper portion is seated flush against and secured to the upper teeth model bracket. Note that this attachment procedure may be readily completed without disturbing the bite positioning.

Ready attachment of the outer plate to the upper teeth model is possible because the position of the outer plate is fully adjustable. This adjustability is provided first by the inner plate being positioned loosely in the post passageway and the lower portion of this passageway being larger than the inner plate. Additionally, the radiused outer end edge of the inner plate insures that this edge does impede any rotational movement of the plate in the slot. Lastly, the open bottom end of the slot allows the inner plate to extent therebeyond if further downward vertical adjustment were required.

A still further advantage is that the system reliably relocates the models in their bite position each time a model is removed and then reattached. Exact relocation results for several reasons. First, the interference fit between the locking tabs on the holding bracket and the indentations the model base prevent model movement and insure exact relative relocation.

Secondly, the structure of the hinge connecting the plates inhibits over stressing of the hinge during upper teeth model movement. For example, the shape of a crown must be checked for anticipated lateral and protrusive jaw movements. To simulate lateral jaw movements the upper model is twisted. This twisting is transferred through the hinge to the inner plate without producing any permanent set to the fixture upper portion. Additionally, it should be understood that while a dental model is not large, it is dense and therefore relatively heavy with respect to the mass of the fixture. The structure of the hinge inhibits any over stressing for this reason as well. It should be understood that if there were any permanent structural deformation, the bite positioning would be distorted.

Lastly, the structural elements of the system may be readily molded in plastic to provide low cost, high volume and high quality production.

DESCRIPTION OF THE DRAWINGS

FIG. 1 is a perspective view of a dental model support system of this invention wherein a dental model set is fitted with respective holding brackets which in turn are secured in a fixture of the system.

FIG. 2 is a side elevation view of the system of FIG. 1.

FIG. 3 is a plan view of an outer plate of an upper portion of the support system fixture.

FIG. 4 is a side elevation view of the outer plate.

FIG. 5 is a plan view of a base portion of the fixture.

FIG. 6 is a cross sectional view of the fixture base portion as seen generally along the line 6—6 in FIG. 5.

FIG. 7 is an end elevation view of the fixture base portion.

FIG. 8 is a plan view of an inner plate of the fixture upper portion.

FIG. 9 is a side elevation view of the inner plate shown with a partial section as would be seen generally along the line 9—9 of FIG. 8.

FIG. 10 is a side elevation view of the holding bracket of the system.

FIG. 11 is a cross sectional view of the holding bracket as seen generally along the line 11—11 in FIG. 10.

FIG. 12 is a plan view of a mold of the system for forming a base of a model of a full jaw impression.

FIG. 13 is a cross sectional view of the mold as seen generally along the line 13—13 in FIG. 12.

FIG. 14 is a plan view of a mold for forming a base of a dental model of a partial impression.

FIG. 15 is an end elevation view of the mold of FIG. 14.

DESCRIPTION OF THE PREFERRED EMBODIMENT

An articular dental model support system of this invention is shown in part in FIGS. 1 and 2 and designated 10. The support system 10 includes a fixture 12 comprising a lower base portion 14 and an upper portion 16.

The base portion 14 is shown in detail in FIGS. 5-7 and has a base plate 18 that connects with an inner support post 20. As best seen in FIGS. 6 and 7, the support post 20 has an upward extending wedge-like shape and is formed with an inner, vertical passageway 22 having a like shape. The passageway 22 has a top opening 24 and a bottom opening 26 which is about half again as wide as the top opening 24.

The upper portion 16 of the fixture 12 is defined by an outer plate 30 and an inner plate 32, see FIGS. 3, 4 and 8, 9. On an inner end 34 of the outer plate 30 is a pair of hinge bearing members 36 separated by a space 38. Each bearing member 36 in turn is formed with a downward facing elongated slot 40.

The inner plate 32 of the fixture upper portion 16 has an outer end radiused edge 42. On an inner end 44 of the inner plate 32 is a hinge pin bracket 46 defined by outer arms 48 and a center arm 50 which carry a pair of spaced apart hinge pins 52. Note that the center of the radius of the inner plate outer end edge 42 is a point 54 defined by an intersection of a longitudinal axis of the pins 52 and the hinge bracket center arm 50. The pins 52 of the inner plate 32 may be pressed through the hinge bearing member slots 40 and secured therein to form a releasable hinge assembly 56.

To use the fixture 12 of the support system 10 to form a crown, denture or other dental appliance for a patient, impressions of a patient's upper and lower teeth are made. Assuming that one or more of the upper teeth are to be crowned, the impression of the lower teeth is filled with uncured gypsum which in turn is placed in contact with like material in a base mold 60 of the system 10. This mold 60 is shown in detail in FIGS. 12 and 13.

The mold 60 has the general shape of a person's jaw and is made of a soft, elastomeric material. The mold 60 has a bottom 62 which is joined by an integrally formed peripheral sidewall 64. On an outer side 66 of the mold bottom 62 is a set of raised ribs 68. The ribs 68 hold the mold 60 above any surface supporting the mold 60 and inhibit adhesion of the bottom 62 to that surface. On an inner side 70 of the mold sidewall 64 is a pair of T-like shaped projections 72 located one each in a front and rear portion 74, 76 of the sidewall 64. These projections 72 form a set of like-shaped indentations 78 in a base 80 of a model 82 of the lower teeth 84 when the material in the mold 60 and the impression of the teeth cures. The physical characteristics of the mold material allows ready removal of a cured model base 80.

As seen in FIGS. 1 and 2, the base 80 of the model 82 of the patient's lower teeth 84 has been fitted into a holding bracket 86 shown typically in FIGS. 10 and 11. The bracket 86 has a center web 88 which connects with spaced apart end walls 90. On an inner side 92 of each end wall 90 is a T-like shaped locking tab 94 sized and positioned to fit complementarily in the indentations 78 of the model base 80.

The bracket 86 is made of plastic so that the end walls 90 are sufficiently resilient to allow the base 80 of the model 82 to be pressed therebetween and currently allow the locking tabs 94 to seat in the model indentations 78. Additionally, the end walls 90 are sufficiently rigid to hold the model base 80 firmly in place. An outer side 98 of the holding bracket center web 88 then is affixed to the base plate 18 of the fixture 12 with a suitable mastic. As affixed, the model 82 of the lower teeth 84 becomes the "opposing" model of the system 10.

A model 102 of the upper teeth 104 is prepared in a similar manner except that a base 106 of the upper teeth model 102 may include a channel (not shown) in which a root portion of certain or all of the upper teeth 104 are secured with dowel pins. For example, where the patent's upper tooth as represented by the tooth 108 in the model 102 requires a crown, this model tooth 108 could be secured to the base 106 by a dowel pin to allow its removal from the model 102. Because the tooth 108 is one of the upper teeth 104, the model 102 is referred to as the "working" model.

Regardless of the exact construction of the upper model 102, its base 106 being formed in the mold 60 has a set of T-like shaped indentations 78 for the locking tabs 94 of a further holding bracket 112. Because the holding brackets 86 and 112 are similar, like reference numbers are used to identify like structure. With the upper teeth model base 106 fitted between the end walls 90 of the holding bracket 112, the upper teeth 104 of the model 102 are placed in contact with the lower teeth 84 of the model 82. The positioning of the upper teeth 104 on the lower teeth 84 must be precise so that the "bite positioning" of the patient's teeth is duplicated as exactly as possible.

Upon completion of this bite positioning, the inner plate 32 of the fixture upper portion 16 is placed in the passageway 22 of the base portion post 20 until its outer end radiused edge 42 contacts the surface on which the fixture 12 is supported. A bottom surface 114 of the outer plate 30 then is swung to contact the outer side 98 of the web 88 of the holding bracket 112. The location of the outer plate 30 then is adjusted to fit flush against the upper holding bracket outer side 98.

This flush positioning may be readily accomplished because the position of the outer plate 30 is fully adjustable. For example, the distance between the base plate 18 and the outer side 98 of the holding bracket 112 typically is different than the length of the inner plate 32. In this case the position of the inner plate 32 is adjusted upward in the passageway 22. Alternately, the inner plate radiused edge 42 be may extended downward through the passageway bottom opening 26, see FIGS. 1 and 2.

Note further that the position of the outer plate 30 may be adjusted to a non-horizontal position with respect to either its longitudinal axis X—X, lateral axis Y—Y or both, see FIG. 1. The hinge assembly 56 provides any required lateral adjustment. The wedge-shaped passageway 22 of the post 20 provides for any required longitudinal adjustment. Also note that the outer end radiused edge 42 of the inner plate 32 facilitates this longitudinal adjustment when the edge 42 is in contact with the support surface. When these adjustments have been made, the outer plate 30 is affixed to the holding bracket 112 and the inner plate 32 is affixed in the post passageway 22 with mastic.

With the holding brackets 86 and 112 affixed to the fixture 12, the working model 102 of the upper teeth 104 may be swung away from the opposing bottom teeth model 82 as required. The length of the hinge assembly 56 with respect to a width of the model 102 inhibits any out-of-balance rotational movement from over stressing the hinge 56. The upper teeth 104 reliably return to their bite position when the upper teeth model 102 is rotated back.

Thus, the tooth 108 to be crowned may be repeatedly shaped and that shape then checked for complementary mating with the interacting lower teeth 84. Checking tooth interaction also includes rotating the upper model 102 about its vertical axis to simulate lateral movements of the jaw. This twisting movement is transferred through the hinge assembly 56 to the upper portion inner plate 32. Note that the inner plate width is less than that of the outer plate 30 to facilitate inner plate twisting. Also, the hinge pins 52 remain firmly seated in the hinge bearing members 36 during this twisting. The inner plate 32 also is sufficiently flexible to simulate protrusive jaw movements.

As required, either or both models 82, 102 may be removed from their respective holding brackets 86, 112 during preparation of a dental appliance. One bracket end wall 90 may include a release tab 116 to facilitate end wall movement and allow the bracket locking tabs 94 to disengage from the model base indentations 78. The T-shape configuration of each facilitates this release. This locking tab-indentation arrangement also insures that any subsequent reattachment of the models 82, 102 to the fixture 12 exactly reproduces the teeth bite positioning.

FIGS. 14 and 15 set out another mold 118. The mold 118 is used to form a base of a model of a partial impression of a patient's teeth. Often times a full model of a patient's teeth is not required to produce the required dental appliance. Because a model of a partial impression is smaller, the resulting smaller model also may be easier with which to work. On an inner side 120 of each end wall 122 of the mold 118 is a T-like shaped projection 124 similar to the projections 72 of the mold 60. The base of a model formed in the mold 118 may be fitted into a bracket similar to the holding brackets 86, 112 and then secured to the fixture 12 in a like manner as described above.

While embodiments, uses, and advantages of this invention are shown and described, it should be understood that this invention is limited only by the claims. Those skilled in the art will appreciate that modifications and changes may be made without departing from the inventive scope and spirit. Any such modification or change may result in further uses and advantages.

What I claim is:

1. An articular support system for a dental model set of upper and lower teeth comprising:
   a fixture having a base portion defined by a base plate connecting with a wedge-like shaped support post, said support post formed with a like-shaped inner vertical passageway, and
   an upper portion comprising an inner plate prepared for insertion in said post passageway though a top opening to fit loosely in said passageway, and an outer plate joined to said inner plate by a hinge, said hinge and said post passageway providing said outer plate with position adjustability,
   wherein a base of said lower teeth model may be affixed to said base portion base plate, said teeth of said upper teeth model may be placed in contact with said teeth of said lower teeth model to create bite positioning between said teeth, said upper portion inner plate may be located in said post passageway and said outer plate may be placed flush against a base of said upper teeth model and affixed thereto regardless of any out-of-level position of said upper teeth model base, and said inner plate may be affixed in said passageway allowing subsequent preparation of dental appliances using said models.

2. An articular support system as defined by claim 1 and further characterized by,
   an edge of an outer end of said upper portion inner plate formed on a radius with a center said radius aligning with a center of said upper portion hinge, wherein said radiused edge of said inner plate may facilitate rotational movement of said outer plate about its longitudinal axis.

3. An articular support system as defined by claim 1 and further characterized by,
   said post passageway having a bottom opening almost twice as wide as said passageway top opening.

4. An articular support system as defined by claim 1 and further characterized by said upper portion hinge comprising,
   a pair of spaced apart hinge bearing members formed on an inner end of said outer plate with each said bearing member having a downward facing elongated slot, and a hinge bracket formed on an inner end of said inner plate, said bracket including end arms and a center arm to hold a set of hinge pins, wherein said hinge pins may be pressed through said bearing member slots and secured by said bearing member in a selectively releasable condition, and said assembled hinge may transfer to said inner plate model simulated lateral and protrusive jaw movements used to check a shape of said dental appliance.

5. An articular support system as defined by claim 4 and further characterized, said hinge having a continuous length about one and one half of a width of said upper teeth model, wherein over stressing of a structure of said hinge is inhibited during rotational movement of said upper teeth model allowing said model to relocate reliably in said bite position.

6. An articular support system as defined by claim 1 and further characterized by, at least one said dental model being fitted into a releasable holding bracket attached to said fixture with mastic means.

7. An articular support system as defined by claim 6 and further characterized by, said holding bracket having end walls formed with locking tabs seated in like-shaped indentations formed in said model base.

8. A system of support for a set of dental models of a patient's upper and lower teeth with at least one said model being a working model, said system comprising:

a fixture having a base portion, an upper portion having an inner plate disposed in slot means of said base portion, said inner plate and said slot means allowing longitudinal and lateral position adjustability of said upper portion, an outer plate connected to said inner plate by hinge means providing said outer plate with positional stability during model movement, and a holding bracket for said working model of said dental model set, said holding bracket having a U-like shape defined by a center web connecting spaced apart end walls formed with inward facing locking tabs forming locking tab-indentation connection means with said working model fitted between said holding bracket end walls, said holding bracket with said working model freely located and attached to said base portion or said upper portion outer plate depending upon which said model is said working model, said attachment occurring upon teeth of said models being in bite registration and said connection means facilitating release of said working model from said holding bracket and promoting reliable restoration of said working model to its previous position in said holding bracket.

9. A method of forming an articular support system for dental models of a patient's upper and lower teeth, said method comprising the steps of:

a. forming a base of each said model in a mold having an inward facing projection on a front and rear portion of a sidewall of said mold to produce likeshaped indentations in each said model base, b. fitting each said model base into a holding bracket having end walls with locking tab that seat respectively in said model base indentations, c. affixing said bracket of said lower teeth model to a base plate of a base portion of a fixture of said system, d. setting said teeth of said upper teeth model on said lower teeth to reproduce a bite positioning of said teeth, e. placing an inner plate of an upper portion of said fixture in a wedge-shaped vertical slot in a support post attached to said base plate, g. positioning an outer plate rotatively attached to said upper portion inner plate flush against said upper teeth model holding bracket, and h. affixing said outer plate to said upper teeth model and affixing said inner plate in said slot, wherein said models may be moved to simulate jaw movements of said patient and thereby check interaction between teeth of said model and an appliance being prepared for said patient with said system reliably returning said teeth of said models to said bite position after said checking movements.

10. A method as defined by claim 9 and further characterized by, said teeth of said model being made from a full impression of said teeth.

11. A method as defined by claim 9 and further characterized by, said teeth of said model being made from a partial impression of said teeth.

* * * * *